US011185528B2

(12) United States Patent
Kolliputi et al.

(10) Patent No.: US 11,185,528 B2
(45) Date of Patent: *Nov. 30, 2021

(54) ALDA-1 TREATMENT AND PREVENTION OF PULMONARY DISEASE

(71) Applicant: University of South Florida, Tampa, FL (US)

(72) Inventors: Narasaiah Kolliputi, Tampa, FL (US); Richard F. Lockey, Tampa, FL (US); Lakshmi Galam, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/839,517

(22) Filed: Apr. 3, 2020

(65) Prior Publication Data

US 2020/0237716 A1 Jul. 30, 2020

Related U.S. Application Data

(62) Division of application No. 16/282,966, filed on Feb. 22, 2019, now Pat. No. 10,660,873.

(60) Provisional application No. 62/634,539, filed on Feb. 23, 2018.

(51) Int. Cl.
| | |
|---|---|
| *A61K 31/357* | (2006.01) |
| *A61P 11/16* | (2006.01) |
| *A61P 11/06* | (2006.01) |
| *A61P 37/08* | (2006.01) |

(52) U.S. Cl.
CPC ............ *A61K 31/357* (2013.01); *A61P 11/06* (2018.01); *A61P 11/16* (2018.01); *A61P 37/08* (2018.01)

(58) Field of Classification Search
CPC .............................. A61K 31/357; A61P 11/00
USPC ........................................................ 435/69.1
See application file for complete search history.

(56) References Cited

U.S. PATENT DOCUMENTS

| | | | |
|---|---|---|---|
| 10,660,873 B2 * | 5/2020 | Kolliputi | ................ A61P 11/06 |
| 2008/0058278 A1 | 3/2008 | Xu et al. | |
| 2010/0113423 A1 | 5/2010 | Mochly-Rosen et al. | |

OTHER PUBLICATIONS

Xu et al. Mitochondrial aldehyde dehydrogenase attenuates hyperoxia-induced cell death through activation of ERK/MAPK and PI3K-Akt pathways in lung epithelial cells. Am. J. Physiol. Lung Cell Mol. Physiol. 291: L966-L975, 2006.*

Perez-Miller, S. et al., Alda-1 is an agonist and chemical chaperone for the common human aldehyde dehydrogenase 2 variant, Nat Struct Mol Biol., Feb. 2010; 17(2): 159-164.

Belmont-Diaz, J. A., et al., Alda-1 modulates the kinetic properties of mitochondrial aldehyde dehydrogenase (ALDH2), The FEBS Journal, 2016, 283: 3637-3650.

Solito, R. et al., Mitochondrial aldehyde dehydrogenase-2 activation prevents beta-amyloid-induced endothelial cell dysfunction and restores angiogenesis, Journal of Cell Science, 2013, 126: 1952-1961.

Stachowicz, A. et al., Mitochondrial Aldehyde Dehydrogenase Activation by Alda-1 Inhibits Atherosclerosis and Attenuates Hepatic Steatosis in Apolipoprotein E-Knockout Mice, Journal of the American Heart Association, 2014, 3: e001329.

Perez, C. et al. Acrolein-Induced Increases in Blood Pressure and Heart Rate are Coupled with Decreased Blood Oxygen Levels During Exposure in Hypertensive Rats. Abstract. Presented at Society of Toxicology Annual Meeting, Mar. 10-14, 2013.

Perez, Christina M. et al. Acrolein inhalation alters arterial blood gases and triggers carotid body-mediated cardiovascular responses in hypertensive rats. Inhal Toxicol. Jan. 2015; 27(1): 54-63. doi:10.3109/08958378.2014.984881.

Fricker, Michael et al. Chronic cigarette smoke exposure induces systemic hypoxia that drives intestinal dysfunction, Feb. 8, 2018; 1-19. https://doi.org/10.1172/jci.insight.94040.

Mach, William J. et al. Consequences of Hyperoxia and the Toxicity of Oxygen in the Lung. Nursing Research and Practice, vol. 2011. Article ID 260482: 1-8. doi:10.1155/2011/260482.

Restriction Requirement dated Jun. 5, 2019 for priority U.S. Appl. No. 16/282,966.

Non-Final Office Action dated Sep. 19, 2019 for priority U.S. Appl. No. 16/282,966.

Lu, Qing, et al. Acrolein Mediates Cigarette Smoke-Induced Increase in Lung Endothelial Cell Permeability and Susceptibility to Acute Lung Injury. American Thoracic Society 2015 International Conference. Am. J. Respir. Crit. Care Med., 2015, 191:A5939.

Lu, Qing, et al. Alda-1 Protects Against Acrolein-Induced Acute Lung Injury and Endothelial Barrier Dysfunction. American Journal of Respiratory Cell and Molecular Biology, 2017; vol. 57 No. 6, pp. 662-673.

* cited by examiner

*Primary Examiner* — Yevgeny Valenrod
(74) *Attorney, Agent, or Firm* — Smith & Hopen, P.A.; Michele L. Lawson

(57) ABSTRACT

Methods of treating or preventing allergic or pulmonary diseases characterized by endothelial dysfunction with Alda-1 are presented. Treatment of pulmonary endothelial cells subjected to hyperoxia with Alda-1 showed an increase in ALDH2 activity and expression. Treatment with Alda-1 also illustrated a decrease in oxidative stress, a decrease in reactive oxygen species (ROS), a decrease in apoptosis, a decrease in inflammation and an enhancement of mitochondrial membrane potential.

10 Claims, 10 Drawing Sheets

JC1 Staining 24hr

Normoxia　　　　Hyperoxia　　　Hyperoxia+Alda

JC1 Staining 48hr

| Normoxia | Hyperoxia | Hyperoxia+Alda |

ALDA-1 TREATMENT AND PREVENTION OF PULMONARY DISEASE

CROSS-REFERENCE TO RELATED APPLICATIONS

This application is a divisional of and claims priority to currently pending U.S. Nonprovisional application Ser. No. 16/282,966, entitled "ALDA-1 Treatment and Prevention of Pulmonary Disease", filed Feb. 22, 2019, which claims priority to U.S. Provisional Patent Application No. 62/634,539, entitled "ALDA-1 Shields Endothelial Cells Against Oxidative Stress Via Activation of ALDH2," filed Feb. 23, 2018, the contents of each of which is incorporated by reference into this disclosure.

GOVERNMENT SUPPORT STATEMENT

This invention was made with government support under Grant No. HL105932 awarded by the National Institutes of Health. The Government has certain rights in the invention.

FIELD OF THE INVENTION

This invention relates, generally, to allergic and/or pulmonary diseases and the treatment of allergic and/or pulmonary diseases. More specifically, it relates to treating endothelial dysfunction and changes in vascular permeability.

BACKGROUND OF THE INVENTION

Endothelial dysfunction and changes in vascular permeability are key events in many allergic diseases including edema and chronic obstructive pulmonary disease (COPD). Mitochondrial dysfunction causes elevation of reactive oxygen species (ROS). ALDH2 (aldehyde dehydrogenase 2) is known to be an effective combatant against mitochondrial dysfunction. Human carriers possessing an inactive ALDH2 variant have been found to be more susceptible to COPD and asthma. However, information pertaining to the ALDH2 interactome is limited.

Aldehyde dehydrogenases (ALDH) constitute a family of enzymes that play a critical role in detoxification of various cytotoxic xenogenic and biogenic aldehydes. ALDH is a key enzyme in fructose, acetaldehyde and oxalate metabolism and represents a major detoxification system for reactive carbonyls and aldehydes. There are at least 19 members/isozymes of the ALDH family, where the various isozymes may exhibit different substrate specificity and/or cellular localization relative to other members of the family.

Cytotoxic aldehydes derive from a variety of sources. For example, environmental (external) sources of aldehydes include those that result from ethanol consumption, from consumption of food sources, from ingestion of hazardous materials such as vinyl chloride, pesticides, herbicides, or from inhalation of hazardous materials such as those found in cigarette smoke, or industrial pollution. Aldehydes, that may be cytotoxic, can also be produced biologically (e.g., endogenously), e.g., as a result of oxidative stress such as occurs in ischemia, irradiation, or metabolism or bioconversion of cellular precursors such as neurotransmitters and drugs. Accumulation of cytotoxic levels of aldehydes, and/or defects in the ALDH enzyme, has been implicated in a variety of diseases and conditions, or in increased risk of disease development. The range of implicated diseases includes neurodegenerative diseases, aging, cancer, myocardial infarction, stroke, dermatitis, diabetes, cataracts, and liver diseases.

Accordingly, what is needed is a therapy targeted towards activation of ALDH2. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

SUMMARY OF THE INVENTION

This summary is provided to introduce a selection of concepts in a simplified form. These concepts are described in further detail in the detailed description of example embodiments of the disclosure below. This summary is not intended to identify key features or essential features of the claimed subject matter, nor is it intended to be used to limit the scope of the claimed subject matter.

The present disclosure provides compounds that function as modulators of aldehyde dehydrogenase 2 (ALDH2) enzymatic activity, as well as compositions and formulations comprising the compounds. The present disclosure provides therapeutic methods involving administering a subject compound, or a subject pharmaceutical composition.

Embodiments disclosed herein include methods of preventing endothelial cell injury from hyperoxic injury. For example, in accordance with one embodiment, administering a therapeutically effective amount of Alda-1 and a pharmaceutically acceptable excipient, reduces damage to endothelial cells from oxidative stress and activates ALDH2. Alda-1 rescues mitochondrial membrane potential; decreases cytochrome C release; suppresses mitochondrial reactive oxygen species production; and preserves mitochondria.

The invention includes a method of treating pulmonary disease characterized by endothelial dysfunction, the method includes the steps of administering a therapeutically effective amount of Alda-1 to a subject suffering from the pulmonary disease characterized by endothelial dysfunction. The Alda-1 activates ALDH2 wherein the Alda-1 reduces damage to endothelial cells from oxidative stress.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
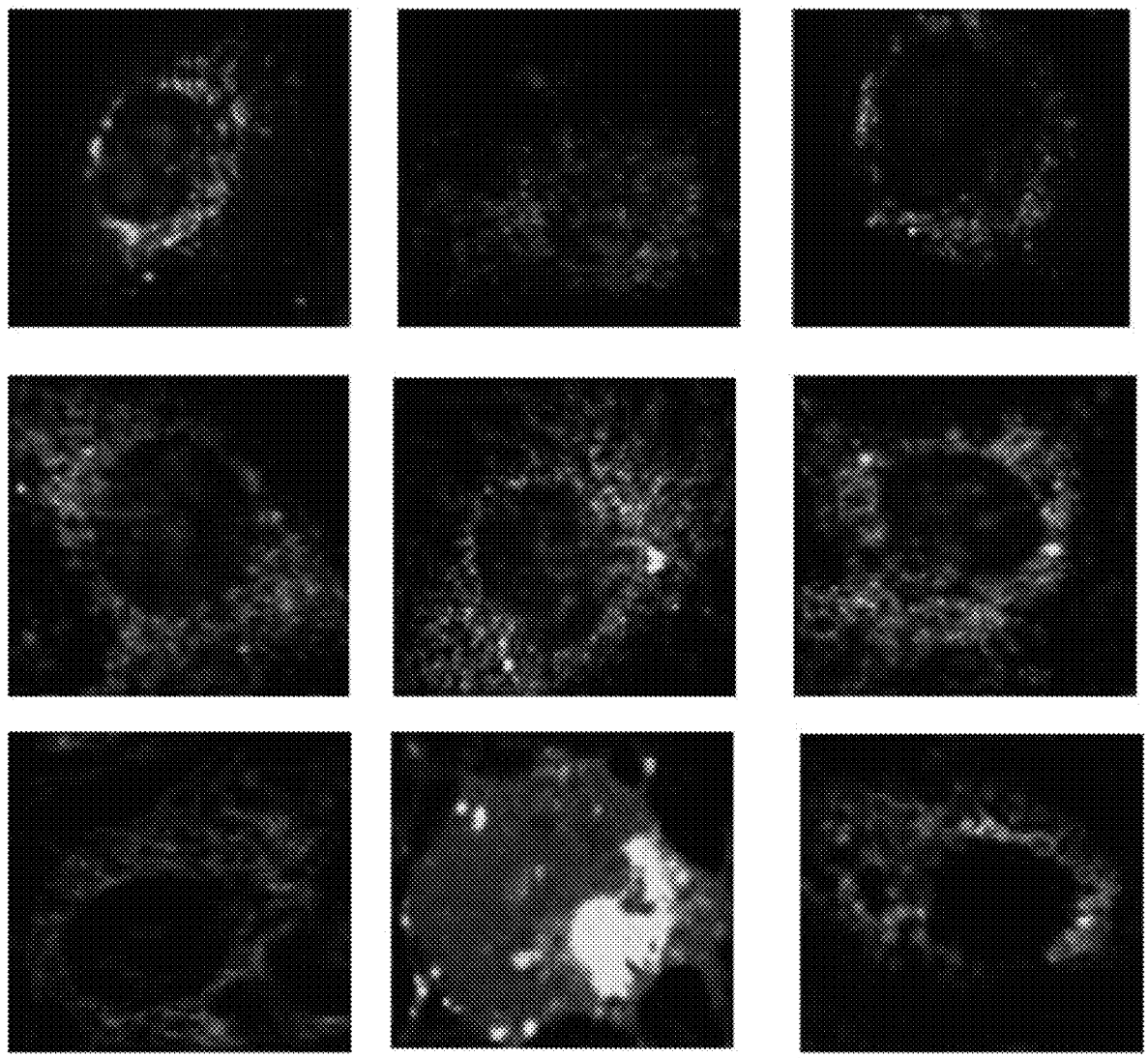
FIG. 1 is a series of MitoSOX images.

In the following detailed description, reference is made to the accompanying drawings, which form a part thereof, and within which are shown by way of illustration specific embodiments by which the invention may be practiced. It is to be understood that other embodiments may be used, and structural changes may be made without departing from the scope of the present application. These embodiments are described in sufficient detail to enable those of ordinary skill in the art to practice the present disclosure, and it is to be understood that other embodiments may be utilized, and that structural, logical, and electrical changes may be made within the scope of the disclosure.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

Any headings used herein should not be considered to limit the scope of embodiments of the invention as defined by the claims below and their legal equivalents. Concepts described in any specific heading are generally applicable in other sections throughout the entire specification.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In an embodiment, the current invention includes an activator of ALDH2, specifically Alda-1, that amplifies ALDH2 activity and attenuates endothelial dysfunction in pulmonary diseases. Alda-1 also known as N-(1,3-Benzodioxol-5-ylmethyl)-2,6-dichlorobenzamid has the empirical formula $C_{15}H_{11}Cl_2NO_3$ with molecular weight 324.16. Alda-1 has structure:

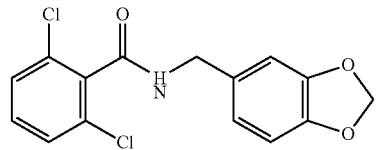 [SMILES: O=C(NCc1ccc2c(c1)OCO2)c1c(Cl)cccc1Cl]

As used herein, the term "aldehyde dehydrogenase" or "ALDH" refers to an enzyme that oxidizes an aldehyde (e.g., a xenogenic aldehyde, a biogenic aldehyde, or an aldehyde produced from a compound that is ingested, inhaled, or absorbed) to its corresponding acid in an NAD+-dependent or an NADP+-dependent reaction. For example, ALDH oxidizes aldehydes derived from the breakdown of compounds, e.g., toxic compounds that are ingested, that are absorbed, that are inhaled, that are produced as a result of oxidative stress, or that are produced during normal metabolism, e.g., conversion of retinaldehyde to retinoic acid. An example of a biogenic aldehyde is acetaldehyde produced as a product of alcohol dehydrogenase activity on ingested ethanol. An aldehyde dehydrogenase can also exhibit esterase activity and/or reductase activity.

The term "ALDH" encompasses ALDH found in the cytosol, in the mitochondria, microsome, or another cellular compartment. The term "ALDH" encompasses ALDH found primarily in one or a few tissues, e.g., cornea, saliva, liver, etc., or in stem cells and embryos. The term "ALDH" encompasses any of the known ALDH isozymes, including ALDH1, ALDH2, ALDH3, ALDH4, ALDH5, etc.

As used herein, the term "mitochondrial aldehyde dehydrogenase-2" or "ALDH2" refers to an enzyme that oxidizes an aldehyde (e.g., a xenogenic aldehyde, a biogenic aldehyde, or an aldehyde produced from a compound that is ingested, inhaled, or absorbed) to its corresponding acid in an NAD+-dependent reaction. For example, ALDH2 oxidizes aldehydes derived from the breakdown of compounds, e.g., toxic compounds that are ingested, that are absorbed, that are inhaled, or that are produced during normal metabolism. Mitochondrial ALDH2 is naturally found in mitochondria.

The term "ALDH2" encompasses ALDH2 from various species. Amino acid sequences of ALDH2 from various species are publicly available. For example, a human ALDH2 amino acid sequence is found under GenBank Accession Nos. AAH02967 and NP-000681; a mouse ALDH2 amino acid sequence is found under GenBank Accession No. NP-033786; and a rat ALDH2 amino acid sequence is found under GenBank Accession No. NP-115792. The term "ALDH2" encompasses an aldehyde dehydrogenase that exhibits substrate specificity, e.g., that preferentially oxidizes aliphatic aldehydes.

The term "ALDH2" as used herein also encompasses fragments, fusion proteins, and variants (e.g., variants having one or more amino acid substitutions, addition, deletions, and/or insertions) that retain ALDH2 enzymatic activity. Specific enzymatically active ALDH2 variants, fragments, fusion proteins, and the like can be verified by adapting the methods described herein. "ALDH2" includes an enzyme that converts acetaldehyde into acetic acid, e.g., where the acetaldehyde is formed in vivo by the action of alcohol dehydrogenase on ingested ethanol.

As used herein, "about" means approximately or nearly and in the context of a numerical value or range set forth means±15% of the numerical. In an embodiment, the term "about" can include traditional rounding according to significant figures of the numerical value.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

As used herein, "treat", "treatment", "treating", and the like refer to acting upon a condition (e.g., endothelial dysfunction) with an agent (e.g., Alda-1) to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as agents which are effective for producing an intended result, including attenuation of endothelial dysfunction. Compositions according to the present invention may be used to effect a favorable change in endothelial dysfunction, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "isolated compound" means a compound which has been substantially separated from, or enriched relative to, other compounds with which it occurs in nature. Isolated compounds are at least about 80%, at least about 90% pure, at least about 98% pure, or at least about 99% pure, by weight. The present disclosure is meant to comprehend diastereomers as well as their racemic and resolved, enantiomerically pure forms and pharmaceutically acceptable salts thereof.

The term "administration" or "administering" is used throughout the specification to describe the process by which a composition comprising Alda-1 as an active agent, are delivered to a patient or individual for therapeutic purposes. The composition of the subject invention and methodology in use thereof can be administered a number of ways including, but not limited to, parenteral (such term referring to intravenous and intra-arterial as well as other appropriate parenteral routes), subcutaneous, peritoneal, inhalation, vaginal, rectal, nasal, or instillation into body compartments.

Administration will often depend upon the amount of compound administered, the number of doses, and duration of treatment. In an embodiment, multiple doses of the agent are administered. The frequency of administration of the agent can vary depending on any of a variety of factors, such as attenuation of endothelial dysfunction and the like. The duration of administration of the agent, e.g., the period of time over which the agent is administered, can vary, depending on any of a variety of factors, including patient response, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

"In combination with," or "co-administration," as used herein, in the context of administering a first compound and at least a second compound, refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same or different routes, and in the same or different dosage form type.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

Acute lung injury (ALI) is caused by lengthened exposure to hyperoxia leading to oxidative stress by crucially impairing the pulmonary function. Mitochondrial dysfunction is a main event in hyperoxic acute lung injury. It is known that hyperoxia causes cellular damage and death by impairing mitochondrial Aldehyde dehydrogenase 2 (ALDH-2) (1) by inducing oxidative stress. It is an object of the current invention to evaluate the effects of Alda-1 on lung endothelial cells during hyperoxic injury.

Example 1—Alda-1-Mediated Modulation of ALDH2 is an Effective Target for Remediation of Endothelial Dysfunction Through Preservation of Mitochondria Materials and Methods Cells obtained were human microvascular endothelial cells (HMVECs). Cell culture medium was EBM-2 containing 10% FBS plus antibiotics. Assays were MitoSOX, JC1, Histology, Western blot, and ALDH2 activity. Antibodies used were mouse anti-ALDH2 antibody, Cytochrome C, and Beclin (cell signaling).

HMVECs were seeded and, after reaching confluence, treated with DMSO and Alda-1. Cells were then exposed to normoxia or hyperoxia at different time points. After 24, 48, and 72 hours, cells were collected for mitochondrial analyses.

Results

Cells treated with Alda-1 displayed elevated ALDH2 activity during both normoxia and hyperoxia. It was also observed that Alda-1 rescued mitochondrial membrane potential, decreased Cytochrome C release, and suppressed mitochondrial ROS production in HMVECs. See FIGS. 1-4.

Figure 2:
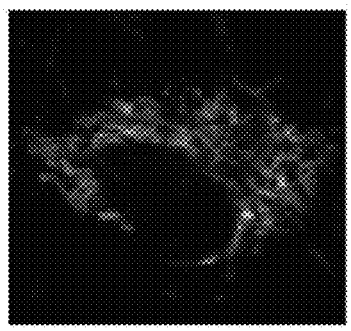
FIG. 2 is a series of images depicting JC1 staining of cells in normoxia, hyperoxia, and hyperoxia with Alda-1 at 24 hours.
Figure 2:
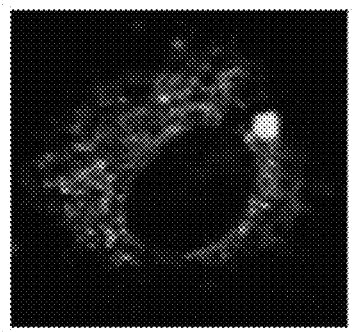
Figure 2:
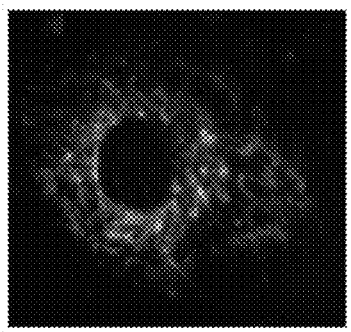
Figure 2:
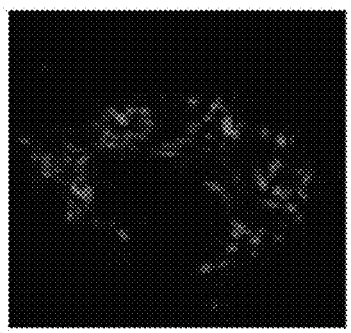
Figure 2:
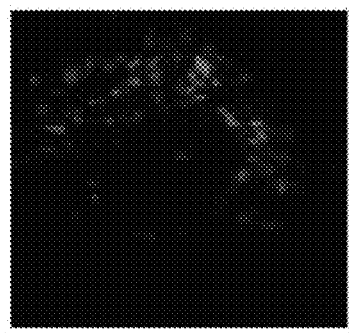
Figure 2:
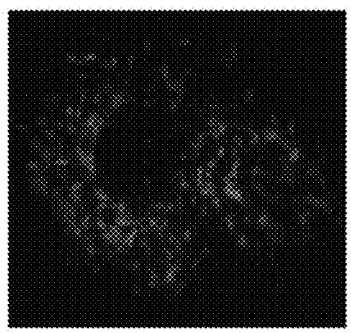
Figure 2:
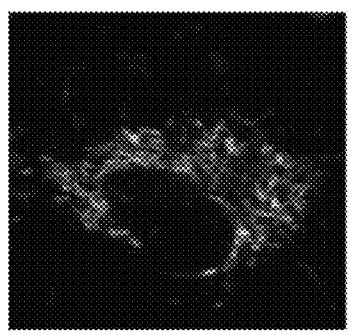
Figure 2:
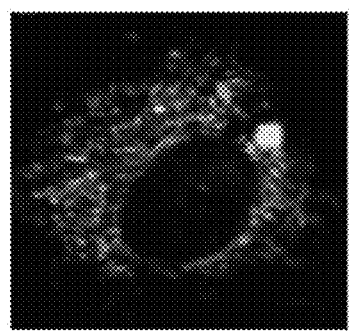
Figure 2:
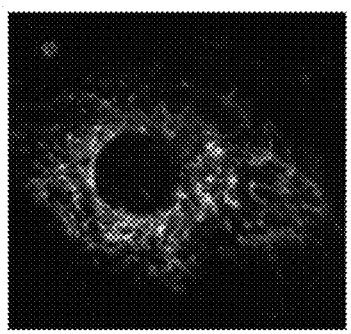
Figure 3:
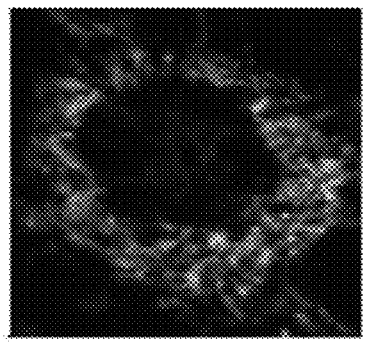
FIG. 3 is a series of images depicting JC1 staining of cells in normoxia, hyperoxia, and hyperoxia with Alda-1 at 48 hours.
Figure 3:
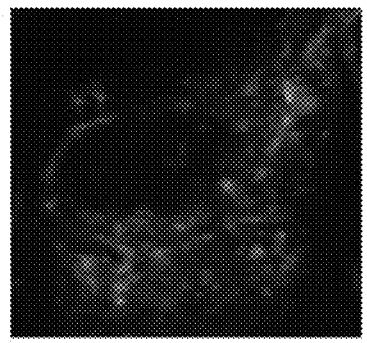
Figure 3:
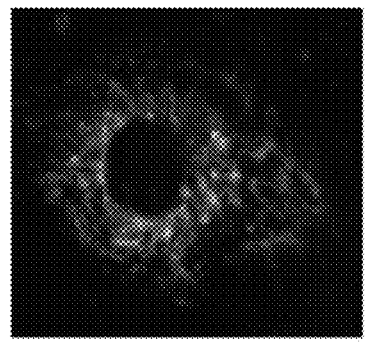
Figure 3:
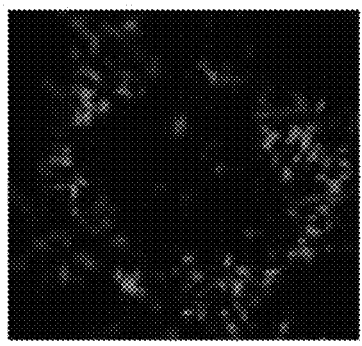
Figure 3:
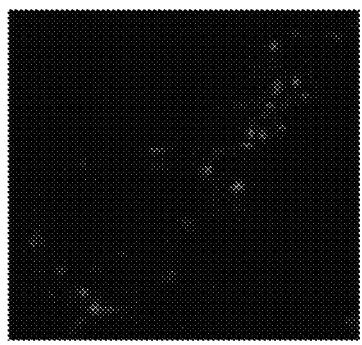
Figure 3:
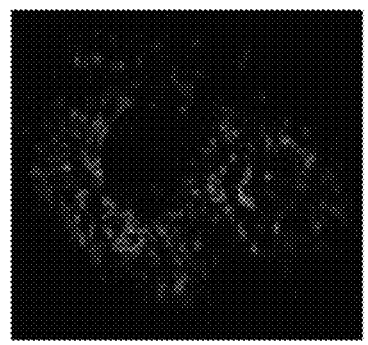
Figure 3:
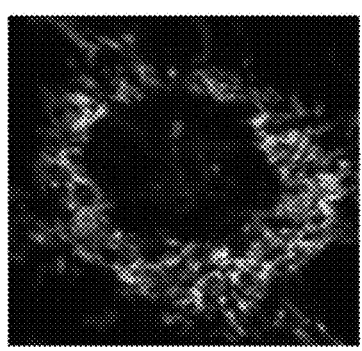
Figure 3:
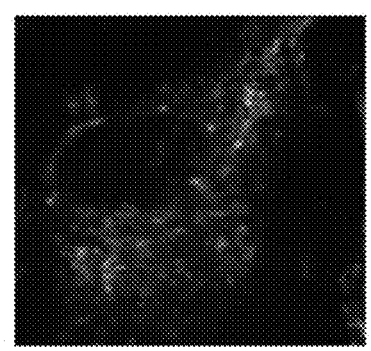
Figure 3:
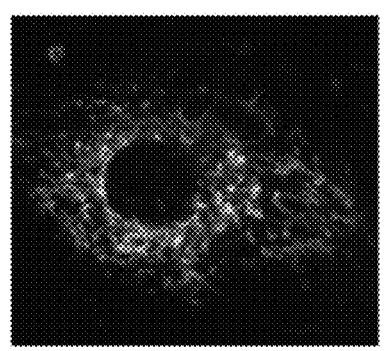
Figure 4:
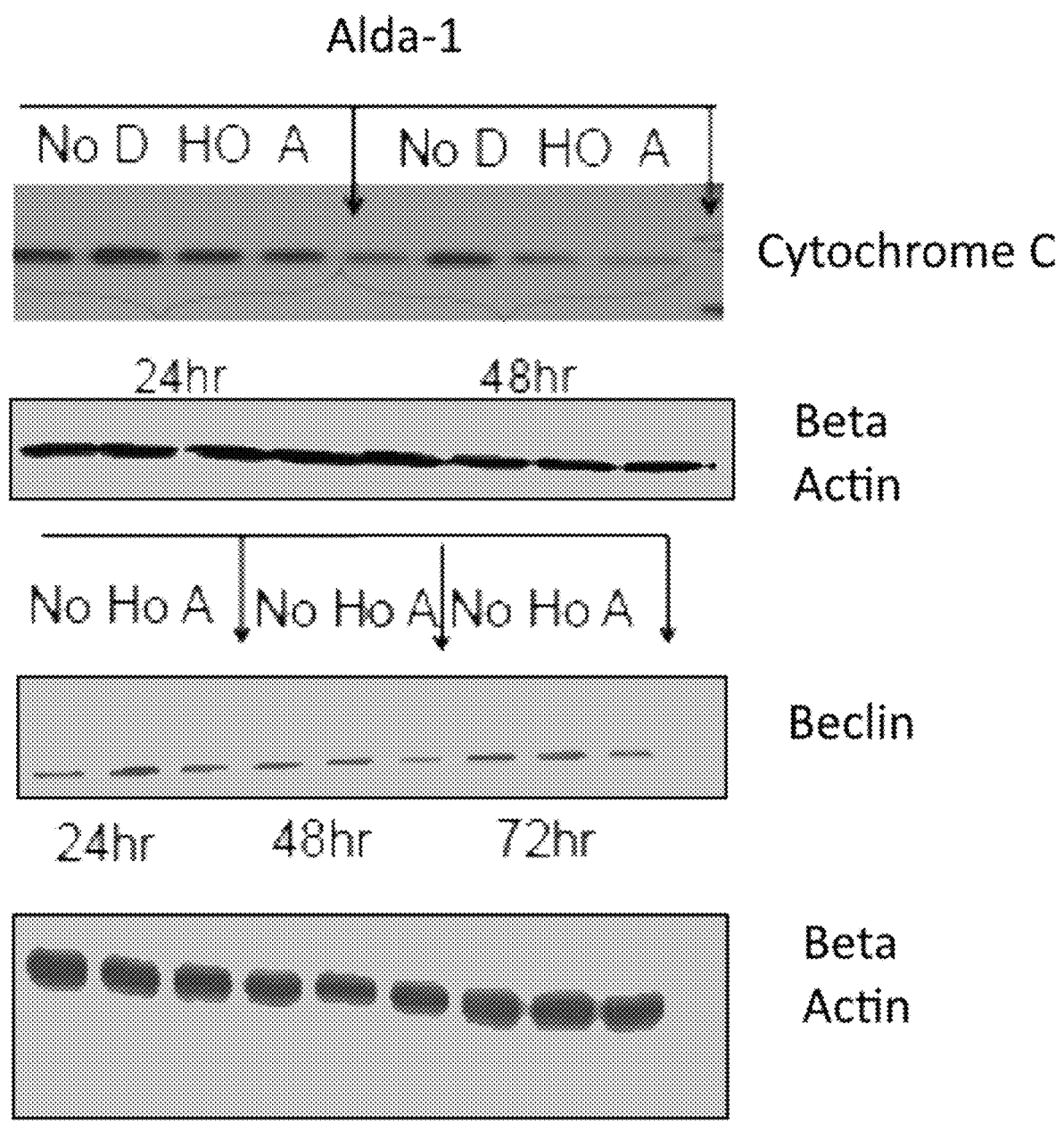
FIG. 4 is a series of images depicting certain results of the present invention from normoxia, hyperoxia, and hyperoxia with Alda-1 on cytochrome C, beta actin, and beclin at 24 hours and 48 hours.

FIG. 1 depicts MitoSOX images. FIG. 2 depicts cells at 24 hours which are exposed to normoxia, hyperoxia, and cells treated with Alda-1. FIG. 3 depicts cells at 48 hours which are exposed to normoxia, hyperoxia, and cells treated with Alda-1. FIG. 4 depicts certain results of the present invention. FIG. 4 depicts normoxia, hyperoxia, and the results of Alda-1 on hyperoxia cells on cytochrome C, Beclin, and Beta actin at 24 hours and 48 hours.

Conclusion

The findings suggest that Alda-1-mediated modulation of ALDH2 is an effective target for remediation of endothelial dysfunction through preservation of mitochondria. These results reveal a promising therapeutic approach to treating allergic diseases where endothelial dysfunction is a characteristic event.

Example 2—Prophetic

It is an object of the current invention to evaluate the effects of Alda-1 on lung endothelial cells in vivo during hyperoxic injury.

Materials and Methods

Lung endothelial cells are treated with Alda-1 and a pharmaceutically acceptable excipient. Cells are then exposed to normoxia or hyperoxia at different time points. After 24, 48, and 72 hours, cells are collected for mitochondrial analyses.

Results

Cells treated with Alda-1 display elevated ALDH2 activity during both normoxia and hyperoxia. It is also observed that Alda-1 rescues mitochondrial membrane potential, decreases Cytochrome C release, and suppresses mitochondrial ROS production in lung endothelial cells.

Example 3—Alda-1 Treatment In Vitro Diminishes the Accumulation of 4HNE and Reduces Oxidative Stress by Decreasing ROS During Hyperoxia The inventors examined the capacity of Alda-1 (benzodioxyl dichlororobezamide) to shield the oxidative stress in HMVEC (2). Briefly, HMVEC pretreated with 20 μM of Alda-1 prior to exposure of hyperoxia show a diminished accumulation of toxic compound 4HNE, a significant decrease in oxidative stress and a significant decrease in apoptotic activity. Furthermore, Alda-1 pretreated samples in hyperoxia show improved Aldh2 activity and ALDH2 expression and significantly enriched mitochondrial membrane potential. Therefore, activation of ALDH2 may inhibit the endothelial dysfunction caused by hyperoxic exposure.

Acute lung injury (ALI) (3) is a serious clinical complication of a respiratory fiasco affecting 200,000 people in US annually (4) with the cases increasing yearly. ALI has caused the death of 70,000 people alone in the USA (5). One type of ALI is acute respiratory distress syndrome (ARDS) of which hyperoxia is an essential part of treatment (6). Routine treatment involves continuous exposure to hyperoxia however, the after-effects of hypoxia treatment are injurious to the patient (7). Prolonged exposure to hypoxia causes hyperoxic acute lung injury (HALI) which eventually leads to death as shown in many animal models. Oxidative stress, ROS and apoptosis caused by hyperoxic exposure leads to dysfunction of endothelial cells (7-9).

HALI has a negligible amount of fibrosis in differentiation when compared to other lung injury models and hyperoxia helps in mimicking ALI (10) (5), thus making focus on the HALI lung injury model attractive. The hyperoxic exposure generates oxidative stress, specially promoting 4HNE, a toxic compound causing harmful effects to mitochondria and impairing cell transduction, (9, 11). 4HNE is a lipid peroxidation product, an ominous reactive aldehyde acting as a biomarker for oxidative stress (8). The oxidative stress-generated 4HNE deploys a harmful impact on a variety of tissues, such as cardiac, neural, epithelial cells, and endothelial cells. (Chen, 2008; Galam, 2015; Neely, 1999; Rahman, 2002; Solito, 2013).

There are various therapies to metabolize oxidative stress, but in lungs ALDH2 acts as a therapeutic agent and also a substrate of 4HNE (9, 12-15). Another remedy for acute lung injury is to diminish 4HNE and ROS by modification of the molecule's membrane receptor px27 (16) and apoptosis signaling kinase (17). The ALDH2 activator Alda-1 has been studied and administration is rarely utilized in experiments (18). The use of Alda-1 has been successfully able to enhance the function of ALDH2 and reduce toxic 4HNE effectively in lung ischemia in epithelial cells, cerebral ischemia, cardiac ischemia, and human umbilical endothelial cells (2, 12, 15, 19)

Until now there have been no studies conducted on human microvascular endothelial cell (HMVEC) in hyperoxia with an Aldh2 activator. The HMVEC play an important role in vascular function and homeostasis in the lungs, and are also involved in remodeling of the vascular wall, angiogenesis, coagulation, blood vessel formation, and acting as an interface for blood circulation (20). HMVECs are vulnerable to oxidative stress and hemodynamic alteration (7). Hyperoxia-caused oxidative stress is a crucial replica that induces the harmful outcome of ALI by obstructing barriers of endothelial and epithelial cells (Galam, 2016). The long term exposure to hyperoxia causes buildup of ROS and affects cell proliferation, cell toxicity and cell viability (7). Therefore, hyperoxia yields a foundation to probe the pathogenesis of cellular damage and pulmonary disease.

The effect of Alda-1 was measured on endothelial cells exposed to hyperoxia to evaluate accumulation of 4HNE in hyperoxia. Due to hyperoxia, oxidative stress is increased which leads to apoptosis. The inventors evaluated the effect of Alda-1 on expression of cytochrome C and Bax in cells exposed to hyperoxia. An increase of 4HNE in HMVEC was shown, indicating that mitochondrial function is affected thus the inventors evaluated the effect of Alda-1 on mitochondria for mitochondrial membrane potential. Further, the effect of Alda-1 on hyperoxia was measured to evaluate the expression and activity of ALDH2. The results showed that Alda-1 reduced accumulation of 4HNE, oxidative stress, apoptosis and enhanced mitochondrial membrane potential and activity of ALDH2 in HMVEC cells exposed to hyperoxia. It is particularly noteworthy that the use of Alda-1 as a treatment in cells exposed to hyperoxia shows that Alda-1 acts as an agonist to ALDH2 to suppress the damage caused by oxidative stress that was induced by hyperoxia(12, 15, 18). Alda-1 treatment provides a replacement remedy for endothelial dysfunction caused by hyperoxic lung injury.

Materials and Methods

Cell Culture

HMVEC's were preserved in EGM-2 MV media (Lonza, Wakersville, Md.) and supplemented with FBS (25 ml), Hydrocortisone (0.2 ml), hFGF-B (2.0 ml), VEGF (0.5 ml), R3 IGF-1 (0.5 ml), Ascorbic acid (0.5 ml), hEGF (0.5 ml), GA-1000 (0.5 ml) at 37° C. in a 5% carbon dioxide-humidified incubator to maintain sufficient cell growth. The cultured cells were validated for confluence (around 70%) and exposed to hyperoxia for 48 hours with and without Alda-1.

Oxidative Stress Assay

The samples of whole cell lysate (50 μg) were seeded in each well. Oxidative stress was measured by an oxiselect 4HNE adduct competitive ELISA kit (Cell Biolabs), according to the instructions of kit.

Western Blot

The HMVEC-L cells were cultured and after reaching confluence (70%), were exposed to hyperoxia with or without Alda-1 for 48 hours. The concentration was determined by the proOX p100 sensor (Biospherix). After hyperoxia, the cell pellets were collected by centrifugation and the cell pellets were suspended in lysis buffer (20 mM Tris HCL, pH7.4, 150 mM Nacl, 0.5% Triton-x 100) and the supernatant was collected after centrifugation at high speed (14000 g) for 15 minutes at 4° C. The amount of protein was calculated by BCA assay kit (Pierce, Rockford, Ill.). Equivalent amount of protein (15 μg) subjected to SDS-PAGE using between 4-20% tris-glycine gel (Bio-rad) after which electro transfer with PVDF membrane was performed, followed by blocking in 5% skim milk with washes with TBST. The membranes were treated with primary and secondary antibodies. The bands were developed by pierce EC1 (Thermo Fischer scientific) and films with protein bands were scanned and analyzed densitometrically by NIH ImageJ software. The ratio of protein to loading control was taken and analyzed in percentages.

JC-1 Staining

HMVEC-L cells were maintained in a EGM-2 (Lonza) media supplemented with FBS (25 ml), Hydrocortisone (0.2 ml), hFGF-B (2.0 ml), VEGF (0.5 ml), R3 IGF-1 (0.5 ml), Ascorbic acid (0.5 ml), hEGF (0.5 ml), GA-1000 (0.5 ml) at 37° C. in a 5% carbon dioxide humidified incubator to maintain a sufficient cell growth. The HMVEC-L cells were plated at density of 1×10,000 cells in a cell view dish with glass bottom (Thomas scientific). When cells attained 70% confluency, they were exposed to hyperoxia for 48 hours with Alda-1 and without Alda-1. Following exposure to hyperoxia, the HMVEC-L cells were washed by HBSS solution (without Ca+ and Mg+) (Gibco). After the washes, the HMVEC-L were treated with JC-1 (5 μM) (Thermo Fisher) at 37° C. for 15 minutes, subsequently washed in HBSS solution three times and placed in the medium. The live cell imaging was conducted using fluorescence microscopy (Olympus). The green and red images were captured in fluorescence and images were quantified by image J by red to green ratio.

ALDH2 Activity

The enzymatic activity of ALDH2 was measured by transformation of acetaldehyde to acetic acid (Chen et al., 2008). The HMVEC-L cells were cultured as mentioned above, followed by 300 µl of buffer (10 mM DTT, 100 mM Tris-HCl pH 8.0, 20% glycerol, 1% Triton X-100) and centrifuged at 55000 g for 30 minutes at 4° C. The supernatant was utilized to detect activity of ALDH2 at 340 nm in a spectrophotometer. The assay mixture (1 ml) contained 10 mM NAD+, 100 mM sodium pyrophosphate, acetaldehyde, water, and 100 µg mitochondrial lysate. The assay activity was started by adding acetaldehyde (10 mM) to the cuvette. The specificity of enzyme reaction was expressed as nmol NADH/minute/mg protein.

Statistical Analysis

All experiments were conducted with 3 samples per group and values were indicated as means±SE. Statistical significance was calculated by using Microsoft Excel with a 2 tailed T-test in which values less than p<0.05 were considered as significant.

Results

Figure 5:
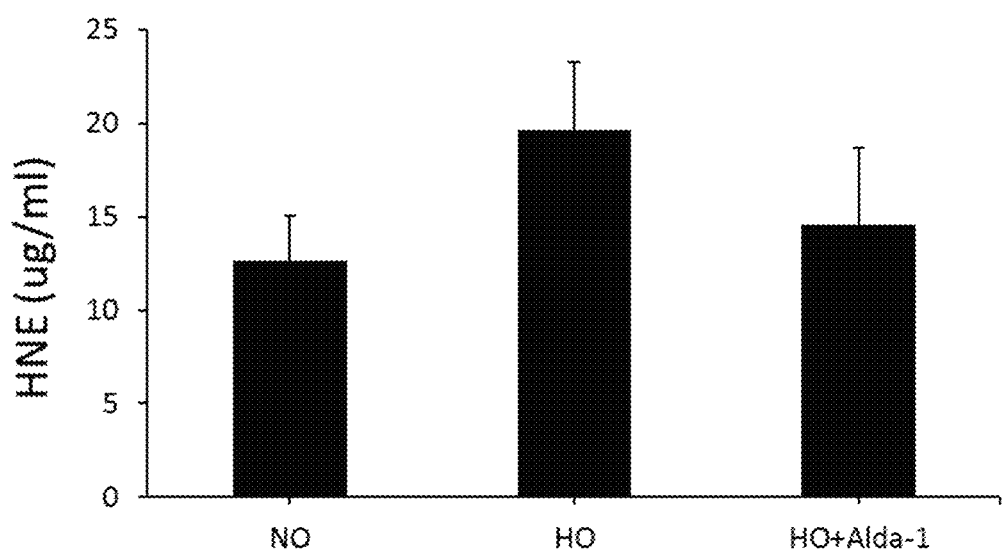
FIG. 5 is an image depicting a graph that representing the whole cell protein lysate for human microvascular endothelial cells under different conditions subjected to ELISA to evaluate the levels of 4HNE content during the Normoxia (NO), hyperoxia (HO), hyperoxia+Alda1 (HO+Alda-1) (20 µM) for 48 hours. The results are shown in mean±SEM.

ALDH2 Activator Attenuates Hyperoxia-Induced 4HNE Accumulation in Pulmonary Endothelial Cells Alda-1 has been shown to protect many different cell types against oxidative stress by increasing ALDH2 activity. However, no study has revealed any similar protective effect of Alda-1 on lung endothelial cells. To verify its antioxidative effect on lung endothelial cells, the inventors exposed human microvascular endothelial cells (HMVEC) to hyperoxic conditions in the presence and absence of Alda-1. The results show that pretreatment with Alda-1 attenuates hyperoxia-induced 4HNE increase in human microvascular endothelial cells. Hyperoxia causes a 55% increase in 4HNE compared to normoxia. Pretreatment of HMVEC with Alda-1 in hyperoxic conditions was shown to cause a 26% decrease in 4HNE accumulation as compared to untreated HMVEC exposed to hyperoxia. These results indicate that ALDH2 plays a vital role in protecting lung vascular endothelial cells from oxidative stress-induced 4HNE upregulation, which is a trigger for cell apoptosis. FIG. 5 shows a graph that represents the whole cell protein lysate for human microvascular endothelial cells (HMVEC) under different conditions in which the cells were subjected to ELISA to evaluate the levels of 4HNE content during the normoxia, hyperoxia, and hyperoxia+Alda1 (20 µM) treatment for 48 hours.

Figure 6A:
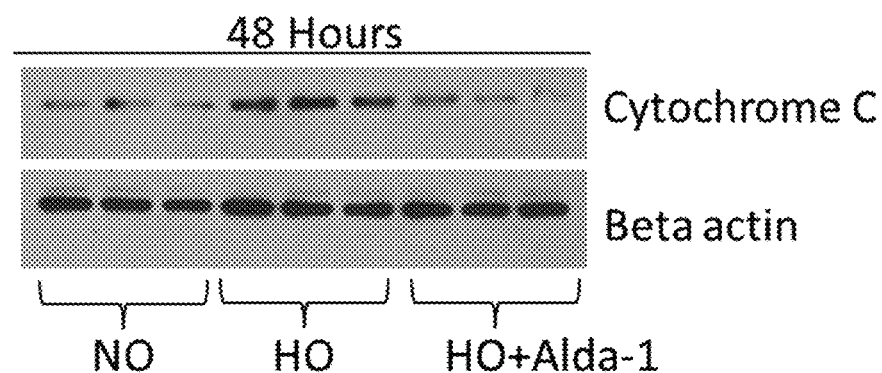
FIG. 6A is an image depicting the western blot analysis of the whole cell lysate for human microvascular endothelial cells under different conditions (n=3) to evaluate the levels of cytochrome C during normoxia, hyperoxia and hyperoxia with Alda-1 (20 µM) for 48 hours. Equal amounts of protein loaded per lane (20 µg).
Figure 6B:
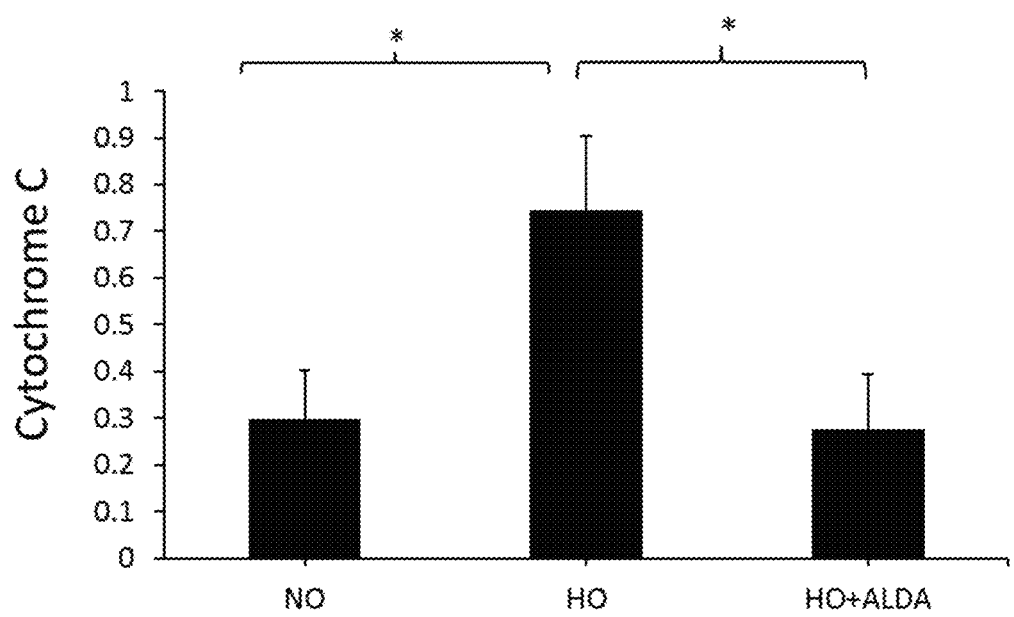
FIG. 6B is a graph depicting expression of Cytochrome C normalized to β-actin and presented in arbitrary units. The results are shown in mean±SEM.

ALDH2 Activator Attenuates Hyperoxia-Induced Downregulation of Oxidative Stress in Pulmonary Endothelial Cells To determine whether ALDH2 activation by Alda-1 suppresses apoptosis signaling caused by oxidative stress in human microvascular endothelial cells, the protein levels of Bax and cytochrome C in whole cell lysate were quantified by western blotting. The results demonstrated that hyperoxia causes a 2.5-fold significant increase in cytochrome C levels and a 1.5-fold increase in BAX levels as compared to normoxia. The pretreatment of HMVEC with Alda-1 in hyperoxia caused a 64% significant decrease in cytochrome C and a 25% significant decrease in Bax as compared to cell exposed to hyperoxia without Alda-1 pretreatment. These results indicate that ALDH2 activation helps to protect human microvascular endothelial cells (HMVEC) from oxidative stress-induced apoptosis. FIG. 6A shows the western blot analysis of the whole cell lysate for HMVEC under different conditions (n=3) to evaluate the levels of cytochrome C during normoxia, hyperoxia and hyperoxia with Alda-1 (20 µM) for 48 hours. Equal amounts of protein were loaded per lane (20 µg). FIG. 6B shows expression of cytochrome C was normalized to β-actin and presented in arbitrary units. The results are shown in mean±SEM.

Figure 7A:
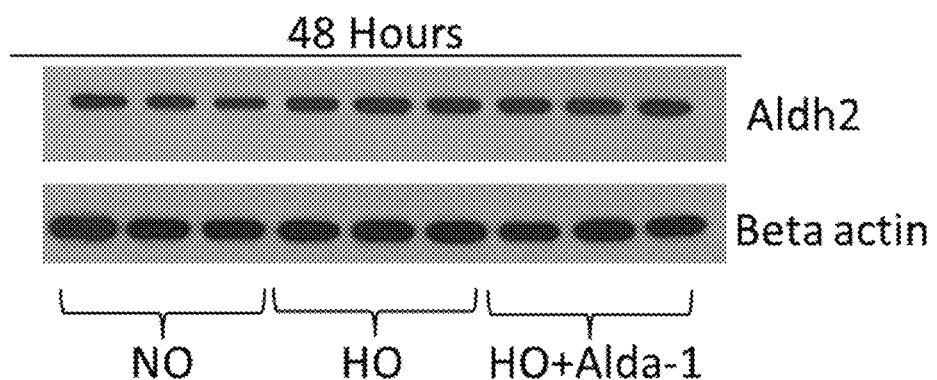
FIG. 7A is an image depicting the whole cell lysate for human microvascular endothelial cells under different conditions (n=3) subjected to immunoblot to evaluate the levels of ALDH2 during normoxia, hyperoxia and hyperoxia with Alda-1 (20 µM) for 48 hours normalized against β-actin. The values indicate standard error mean (*P<0.05). Equal amounts of protein loaded per lane (20 µg).
Figure 7B:
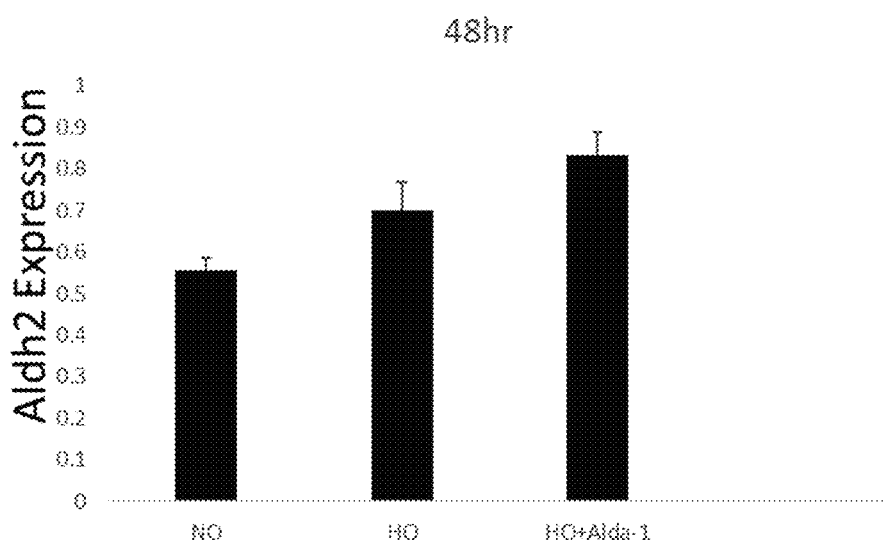
FIG. 7B is a graph depicting expression of ALDH2 normalized to β-actin and presented in arbitrary units. The results are shown in mean±SEM.

ALDH2 Activator does not Promote Hyperoxia-Induced Expression of ALDH2 in Pulmonary Endothelial Cells In the existing literature, Alda-1 treatment has been shown to have no impact on the expression of ALDH2 expression in in vitro in many different cell types. Moreover, no study has been conducted to reveal the expression of ALDH2 in lung microvascular endothelial cells. To confirm the effect of Alda-1 on ALDH2 expression, the protein level of ALDH2 in whole cell lysate was evaluated by western blotting. The results suggests that pre-treatment with Alda-1 in hyperoxia has no effect on ALDH2 expression in hyperoxia treatment. These results indicate that pretreatment with an ALDH2 activator does not alter the expression of ALDH2 during hyperoxia in human microvascular endothelial cells. FIG. 7A is an image that depicts the whole cell lysate for human microvascular endothelial cells under different conditions (n=3) subjected to immunoblot to evaluate the levels of ALDH2 during normoxia, hyperoxia and hyperoxia with Alda-1 (20 µM) for 48 hours normalized against β-actin. The values indicate standard error mean (*P<0.05). Equal amounts of protein loaded per lane (20 µg). FIG. 7B is a graph showing expression of ALDH2 was normalized to β-actin and presented in arbitrary units. The results are shown in mean±SEM.

Figure 8A:
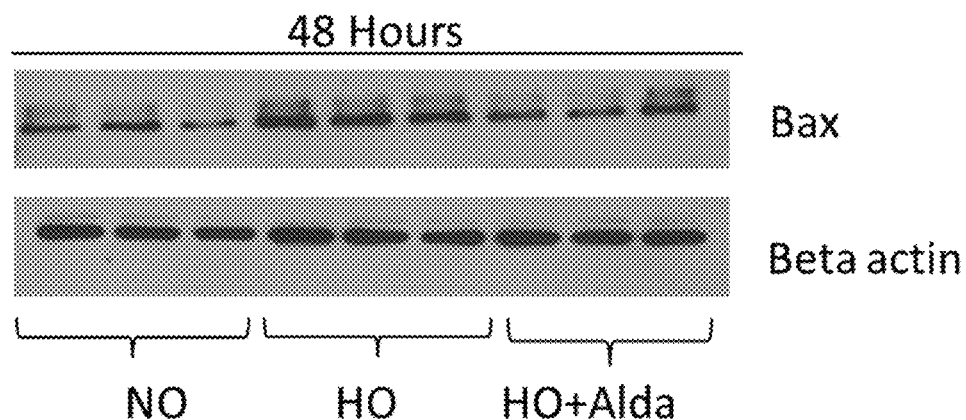
FIG. 8A is an image depicting the whole cell lysate for human microvascular endothelial cells under different conditions (n=3) subjected to immunoblot to evaluate the levels of Bax during normoxia, hyperoxia and hyperoxia with Alda-1 (20 µM) for 48 hours normalized against Beta actin. The values indicate standard error mean (*P<0.05). Equal amounts of protein loaded per lane (20 µg).
Figure 8B:
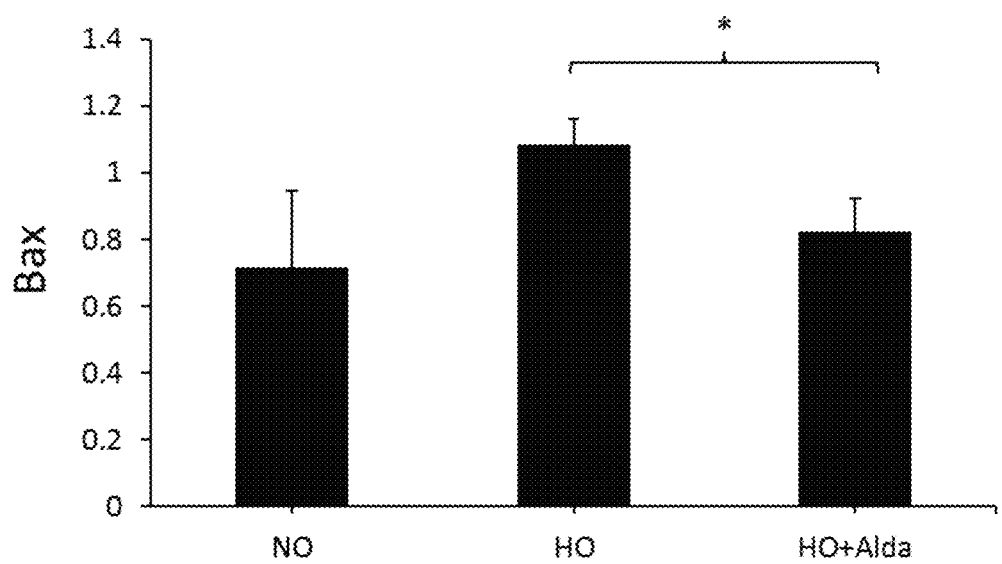
FIG. 8B is a graph depicting expression of Bax normalized to β-actin and presented in arbitrary units. The results are shown in mean±SEM.

ALDH2 Activator Promotes Hyperoxia-Induced ALDH2 Activity in Pulmonary Endothelial Cells To evaluate whether the ALDH2 activator Alda-1 enhances ALDH2 activity during hyperoxia in human microvascular endothelial cells, the mitochondrial extract was isolated and an ALDH2 activity assay was conducted. The results demonstrated that hyperoxia with Alda-1 treatment caused a 45% increase in ALDH2 expression compared to hyperoxia without Alda-1 pretreatment. These results indicate that the ALDH2 activator Alda-1 increases the activity of ALDH2 under hyperoxia in human microvascular endothelial cells. FIG. 8A is an image depicting the whole cell lysate for human microvascular endothelial cells under different conditions (n=3) subjected to immunoblot to evaluate the levels of Bax during normoxia, hyperoxia and hyperoxia with Alda-1 (20 µM) for 48 hours normalized against β-actin. The values indicate standard error mean (*P<0.05). Equal amounts of protein were loaded per lane (20 µg). FIG. 8B is a graph depicting expression of Bax normalized to β-actin and presented in arbitrary units. The results are shown in mean±SEM.

Figure 9A:
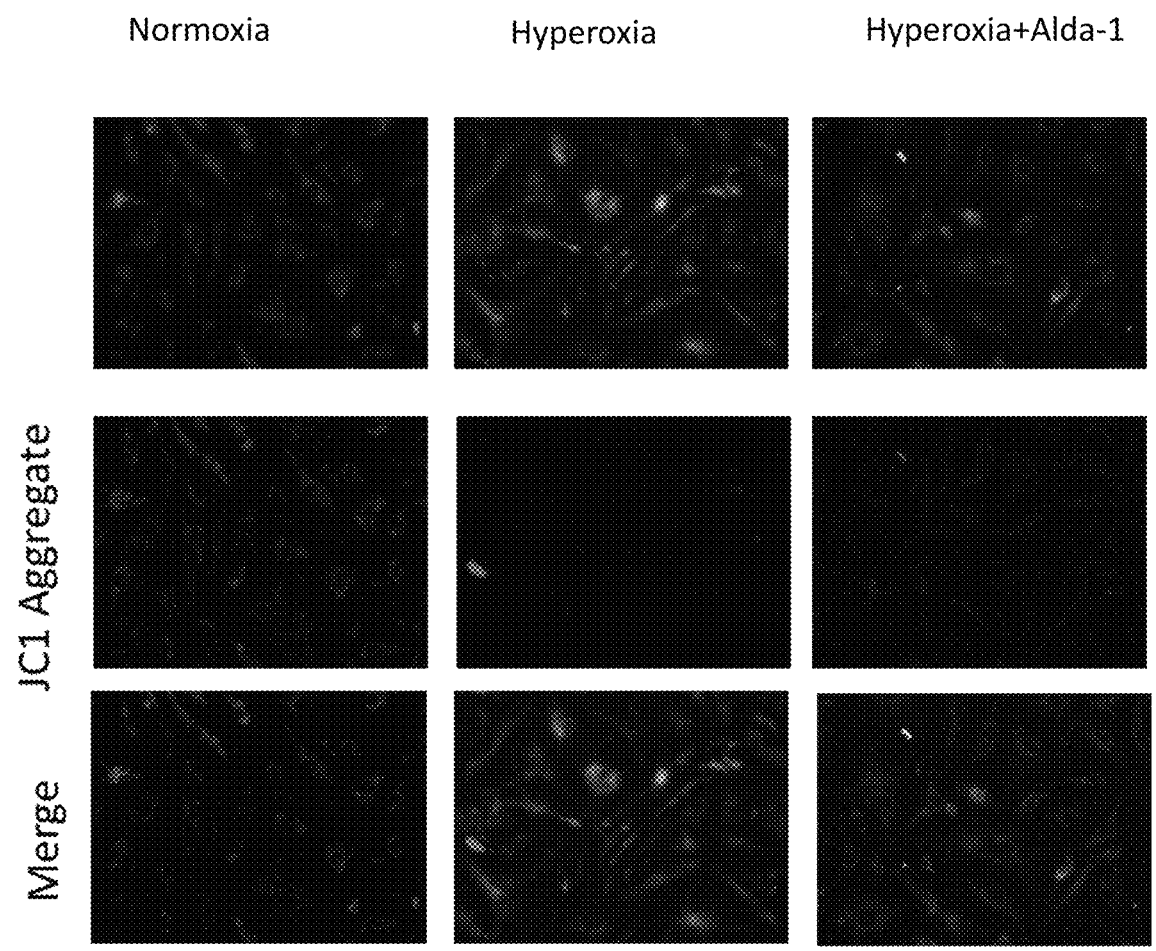
FIG. 9A is an image depicting the human microvascular endothelial cells under different conditions subjected to the JC1 staining to evaluate the mitochondrial membrane potential during normoxia, hyperoxia and hyperoxia with Alda-1 (20 µM) for 48 hours. The values indicate standard error mean (*P<0.05).
Figure 9B:
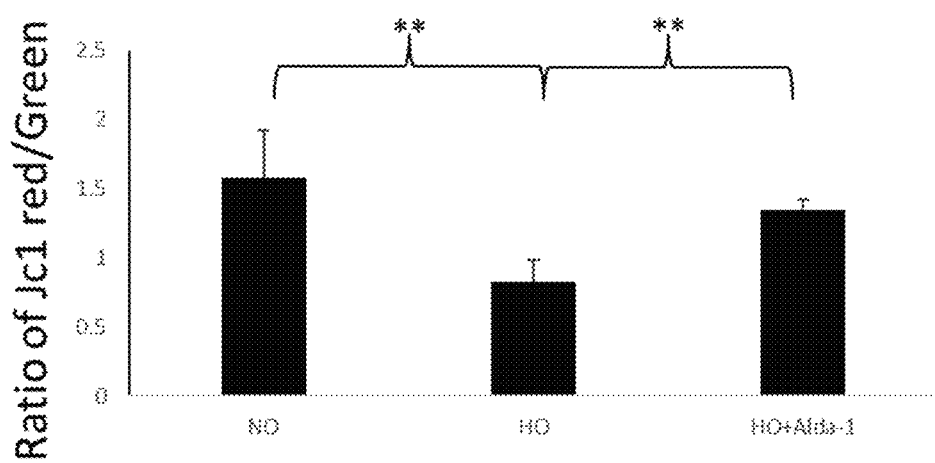
FIG. 9B is a graph depicting the Jc1 images from FIG. 9A quantified using imageJ software with an intensity expressed in arbitrary units. The results are shown in mean±SEM (Magnification=200×).

ALDH2 Activator Promotes the Hyperoxia-Induced Mitochondrial Membrane Potential in Pulmonary Endothelial Cells To evaluate the effect of Alda-1 during hyperoxia on human microvascular endothelial cells, the mitochondrial membrane potential was quantified by JC-1. JC-1 is considered to be an indicator of cellular damage and cell death. The cellular damage can be attributed by decrease in fluorescence as a red to green ratio. The results demonstrated that membrane potential exhibited a 1.90-fold increase in normoxia compared to hyperoxia and a 1.62-fold increase in hyperoxia with Alda-1 treatment compared to hyperoxia without Alda-1 treatment. These results suggest that the ALDH2 activator, Alda-1, decreases cellular damage during hyperoxia in human microvascular endothelial cells (P<0.005). FIG. 9A shows the human microvascular endothelial cells under different conditions subjected to the JC1 staining to evaluate the mitochondrial membrane potential during normoxia, hyperoxia and hyperoxia with Alda-1 (20 µM) for 48 hours. The values indicate standard error mean (*P<0.05). FIG. 9B is a graph depicting Jc1 images quantified using imageJ software with an intensity expressed in arbitrary units. The results are shown in mean±SEM (Magnification=200×).

Hyperoxia exposure causes cellular dysfunction in HMVECs, and prolonged exposure to hyperoxia causes organ failure (7). During hyperoxic exposure, the cell undergoes oxidative stress due to an increase in ROS (21). Although Alda-1 has been shown to reduce injuries in the heart, liver, brain, kidney, and intestines, it has not previously been thoroughly tested in the lung (12, 22-25). ALDH2 has also been implicated in numerous pathologies, such as ischemia, Alzheimer's disease, and Parkinson disease. The use of Alda-1 has been proven to attenuate endothelial cell injuries in neural and umbilical cells. For the first time, the inventors have demonstrated that the use of Alda-1, an ALDH2 activator, is capable of attenuating endothelial dysfunction in pulmonary human microvascular endothelial cells (HMVECs) during hyperoxia. Mitochondrial ALDH2 plays a pivotal role in preventing the accumulation of 4HNE (15, 18), preventing the accumulation of oxidative stress (8), preventing expression of apoptotic marker, and enhancing mitochondrial membrane potential (15, 26).

It has been effectively shown that in vitro exposure to hyperoxia causes an accumulation of the toxic compound 4HNE which causes excessive alveolar protein leaking, and pulmonary edema, both of which contribute to ALI (26). For the first time the inventors provide evidence that 4HNE causes extensive damage in HMVECs. The inventors pretreated HMVECs with Alda-1, exposed them to 48 hours of hyperoxia and showed that hyperoxic exposure caused an accumulation of 4HNE, but that treatment with Alda-1 reduced that amount. Hyperoxic exposure in vivo has been shown to increase the formation of adducts of 4HNE (27). Moreover, these protein alterations result in impaired cellular feedback, thereby causing the production of ROS and oxidative stress, which ultimately leads to cellular dysfunction and death (8, 16).

The exposure of pulmonary cells to hyperoxia for prolonged durations causes damage to epithelial and endothelial cell barriers, thereby increasing ROS, oxidative stress, and apoptosis, and decreasing the mitochondrial membrane potential (9, 28). Hyperoxia also causes an increase in 4HNE levels affecting mitochondrial membrane potential. These changes occur within 48 hours of exposing HMVECs to hyperoxia. The disaggregation and death of HMVEC can be seen in hyperoxia (FIG. 5). The increase in mitochondrial membrane potential, ALDH2 activity and ALDH2 expression of HMVECs pretreated with Alda-1 (FIGS. 9A, 10 and 7A respectively) shows mitochondrial oxidative stress induced by hyperoxia.

Figure 10:
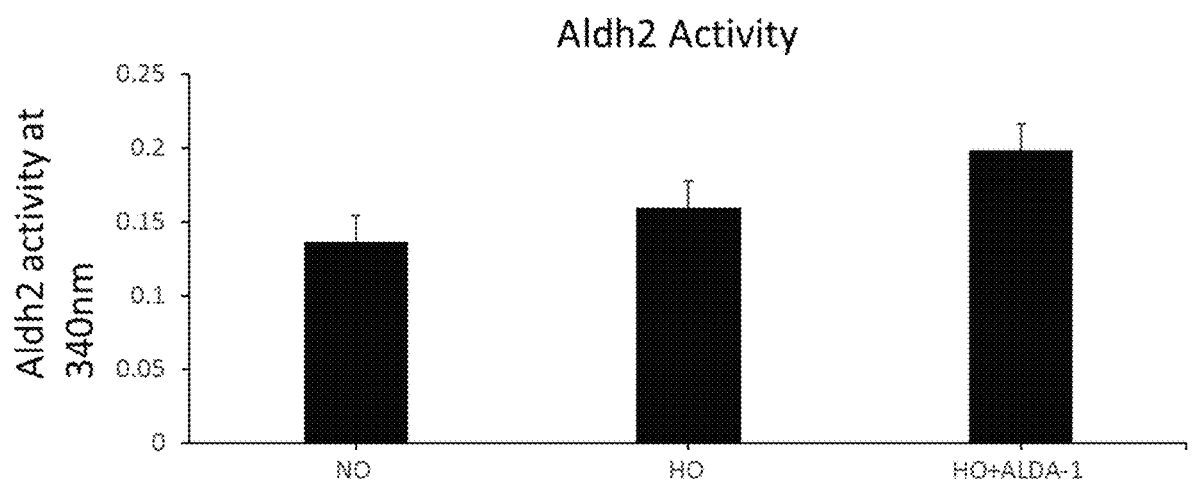
FIG. 10 is a graph depicting the mitochondrial lysate for the human microvascular endothelial cells under different conditions (n=3) subjected to enzymatic assay to evaluate the ALDH2 activity at 340 nm during normoxia, hyperoxia and hyperoxia with Alda-1 (20 uM) for 48 hours.

For the first time, the inventors have revealed that, in HMVECs exposed to hyperoxia, ALDH2 activity and ALDH2 expression increase as a result of the Alda-1 treatment during hyperoxia (FIGS. 7A and 10). When treated with Alda-1 prior to the hyperoxia exposure, the recovery of Aldh2 decreased cytochrome C release and repaired mitochondrial membrane potential (FIGS. 6A and 9A). Alda-1 provided powerful protection against the effects of hyperoxia in HMVECs, as shown by the diminished levels of Bax, an apoptotic activator indicative of mitochondrial stress (FIG. 8A). The importance of Alda-1 shielding ALDH2 against these disastrous effects has been profoundly described by Perez Miller et al.

The inventors demonstrate for the first time the protective effects of Alda-1 in HMVECs undergoing 48 hours of hyperoxic exposure. The pretreatment of Alda-1 before hyperoxic exposure caused a decrease in 4HNE levels versus HMVECs that were exposed to hyperoxia alone (FIG. 5). This decrease is believed to be because ALDH2, which has increased activity in cells treated with Alda-1, converts 4HNE into acetaldehyde, which is then converted into acetic acid by ALDH2 as well (Xu, Guthrie et al. 2006). There was no change in the expression of ALDH2 in the group treated with DMSO or Alda-1 prior to hyperoxia exposure (FIG. 7). The hyperoxic ALDH2 expression levels were high when compared to normoxia because ALDH2 exerts protective effects during hyperoxic exposure, thereby leading to its natural overexpression. Overall, Alda-1 was successfully able to enhance the activity of ALDH2 in hyperoxic conditions to relieve oxidative stress. Literature shows that ALDH2 is a critical protein in numerous tissues, such as liver, heart, muscle, and kidney (30), and for the first time the inventors demonstrate its importance in lung tissues, namely Human Lung Microvascular Endothelial cells.

Conclusion

The inventors have shown that hyperoxic damage can be guarded by ALDH2 activation via pretreatment with Alda-1. For the first time the effects of Alda-1 in human microvascular endothelial cells during hyperoxia have been shown. It has been shown that treatment with Alda-1 diminishes the accumulation of 4HNE and reduces oxidative stress by decreasing ROS during hyperoxia. Hyperoxia has been shown to elevate oxidative stress, depolarize the mitochondrial membrane, decrease ALDH2 activity, disrupt cellular transduction, and cause apoptosis. The use of Alda-1 reversed the harmful effects of hyperoxic injury to HMVECs, revealing that oxidative stress is important in the pathological processes of various diseases associated with the lung and endothelial cells. Therefore, administration of Alda-1 may act as a novel therapeutic drug to mitigate hyperoxic injury in lungs.

Example 4—Alda-1 Treatment Maintains Mitochondrial Homeostasis and Reduces Immune Cell Infiltration In Vivo Acute respiratory distress syndrome (ARDS) is associated with fluid filled lungs and hypoxia. Accordingly, ARDS patients are placed on supplemental oxygen; however, hyperoxia can damage the lungs, cause mitochondrial dysfunction, and ultimately lead to acute lung injury in animal models of ARDS. Mitochondrial aldehyde dehydrogenase 2 (ALDH2) metabolizes dangerous, reactive products, such as 4-hydroxynonenal (4HNE), that otherwise causes oxidative stress. The inventors examined whether Alda-1, an ALDH2 activator, enhances the activity of ALDH2, thus alleviating hyperoxia damage by preventing mitochondrial dysfunction and reducing immune cell infiltration. The inventors also examined if administration of Alda-1 recovers mitochondrial dynamics and reduces cytokine levels and immune cell infiltration.

Methods

C57BL/6 mice were exposed to hyperoxia for 48 hours with DMSO (Control) and Alda-1 (20 mM) via alzet pumps on the dorsal side of mice. The mice were divided into four groups: normoxia+DMSO (room air), normoxia+Alda-1, hyperoxia+DMSO, and hyperoxia+Alda-1. The lungs were harvested and the bronchoalveolar lavage (BAL) fluid was collected and analyzed by immunoblot and cytokine levels.

Results

Immunoblot analysis of lung lysate demonstrated that mice treated with Alda-1, compared to mice treated with DMSO, during hyperoxia have decreased levels of OPA1 and Drp1, indicating that Alda-1 shields against oxidative stress for proteins associated with mitochondrial dynamics. Moreover, the BAL fluid analysis reveals less infiltration of macrophages in mice treated with Alda-1 versus mice treated with DMSO alone. These results indicate that activation of ALDH2 via Alda-1 is protective against hyperoxia-induced acute lung injury and may be a viable therapeutic agent for ARDS.

Conclusion

These findings suggest that Alda-1, an ALDH2 activator, maintains mitochondrial homeostasis and reduces immune cell infiltration in this mouse model of ARDS and may be a novel therapeutic agent in ARDS.

Example 5—Alda-1 Reduces the Effects of ALI Induced by Hyperoxia by Protecting Mitochondrial Dynamics In Vivo Acute Lung Injury (ALI) is characterized by acute and severe inflammation of the lungs that can result in respiratory failure. The main symptom of ALI is shortness of breath associated with low oxygen. It is characterized by X-ray findings of bilateral pulmonary infiltrates. The most common treatment for ALI is to provide supplemental oxygen, which can lead to the accumulation of reactive oxygen species (ROS) and the toxic metabolite 4-hydroxy-2-noneal (4HNE). This leads to further oxidative stress, thus limiting cell proliferation and triggering aberrations in mitochondrial dynamics. Mitochondrial dysfunction is one of the hallmarks of ALI. Mitochondrial Aldehyde dehydrogenase 2 (ALDH2) acts as a mitochondrial shield against damage. Activation of ALHD2 via Alda-1 also can attenuate the mitochondrial damage during hyperoxic exposure. This example is focused on the therapeutic potential of Alda-1 to reduce the effects of hyperoxic exposure in ALI by protecting mitochondrial dynamics.

Methods

C57BL/6 mice were pretreated with DMSO (control) and 20 μM Alda-1 (administered via Alzet pumps), then exposed to hyperoxia for 48 hours. The mice were divided into three groups: Room air, hyperoxia (48 hour)+DMSO, and hyperoxia (48 hour)+Alda-1. The lung tissues were harvested, and lysates evaluated by immunoblot analysis.

Results

Western blot analysis of lung lysates indicates that mice treated with Alda-1 during hyperoxia versus mice treated only with hyperoxia have decreased levels of mitochondrial fusion proteins mitofusin 1 (MFN1) and mitofusin 2 (MFN2) relative to mice that were not treated. In addition, mitophagy protein PTEN-induced kinase 1 (PINK1) levels also decrease in mice treated with Alda-1 prior to hyperoxia exposure compared to hyperoxic controls. These data suggest that Alda-1 protects mitochondria against hyperoxia-induced damage by maintaining mitochondrial homeostasis.

Conclusion

These findings suggest that Alda-1 may be a treatment option to regulate the mitochondrial dynamics via activation of the mitochondrial enzyme Aldehyde dehydrogenase 2 (ALDH2).

Example 6—Alda-1 Reduces the Effects of ALI In Vivo

Acute lung injury (ALI) is a critical lung disorder where the inefficient oxygen uptake causes acute hypoxemia and Acute Respiratory Distress Syndrome (ARDS). There are nearly 200,000 annual cases of ALI in the United States alone, and the incidence rate is increasing. At the molecular level, hyperoxic exposure causes an increase in reactive oxygen species, leading to an accumulation of 4-Hydroxy-2-nonenal (4HNE), a lipid peroxidation product causes protein adducts and inhibits the activity of the mitochondrial enzyme ALDH2 (Aldehyde dehydrogenase), which is involved in metabolism of alcohol. Use of Alda-1 may reduce the effect of acute lung injury.

Methods

The C57BL/6 mice were embedded with osmotic pumps and continuously injected with either DMSO or Alda-1 (20 μM), then they were exposed to 100% oxygen 48 hours. The lung samples, as well as Bronchial Alveolar Lavage Fluid, were collected for the evaluation of infiltration of cytokines, inflammation, autophagy, and apoptosis by Diff Kwik staining, H&E staining, and western blot.

Results

The mice treated with DMSO in hyperoxia showed more cytokine and neutrophil infiltration and elevated inflammation than mice treated with Alda-1 in hyperoxia. The western blot analysis of Alda-1-treated mice showed reduced cytochrome C release, reduced LC3B, and reduced NF-κB-p65, while also showing a decrease in oxidative stress, inflammation and autophagy.

The findings imply that Alda-1, an ALDH2 activator is a potential therapeutic drug for the treatment of acute lung injury.

Conclusion

The inventors have shown, both in vitro and in vivo, that hyperoxic damage can be prevented and treated by administration of Alda-1. Treatment of endothelial dysfunction in pulmonary HMVECs due to hyperoxia, as well as in mice exposed to hyperoxia, with Alda-1 diminishes the accumulation of 4HNE and reduces oxidative stress by decreasing ROS during hyperoxia. Treatment with Alda-1 reversed the harmful effects of hyperoxic injury and enhanced the mitochondrial membrane, increased ALDH2 activity, and decreased apoptosis. Therefore, administration of Alda-1 acts as a novel therapeutic drug to mitigate hyperoxic injury in lungs.

REFERENCES

1. Guo J M, Liu A J, Zang P, Dong W Z, Ying L, Wang W, et al. ALDH2 protects against stroke by clearing 4-HNE. Cell research. 2013; 23(7):915-30.
2. Ding J, Zhang Q, Luo Q, Ying Y, Liu Y, Li Y, et al. Alda-1 Attenuates Lung Ischemia-Reperfusion Injury by Reducing 4-Hydroxy-2-Nonenal in Alveolar Epithelial Cells. Critical care medicine. 2016; 44(7):e544-52.
3. Zarkovic N. 4-hydroxynonenal as a bioactive marker of pathophysiological processes. Molecular aspects of medicine. 2003; 24(4-5):281-91.
4. Cox R R, Jr., Phillips O, Kolliputi N. Putting the brakes on acute lung injury: can resolvins suppress acute lung injury? Frontiers in physiology. 2012; 3:445.
5. Cox R, Jr., Phillips O, Fukumoto J, Fukumoto I, Parthasarathy P T, Arias S, et al. Enhanced Resolution of Hyperoxic Acute Lung Injury as a result of Aspirin Triggered Resolvin D1 Treatment. American journal of respiratory cell and molecular biology. 2015; 53(3):422-35.
6. Fukumoto J, Fukumoto I, Parthasarathy P T, Cox R, Huynh B, Ramanathan G K, et al. NLRP3 deletion protects from hyperoxia-induced acute lung injury. American journal of physiology Cell physiology. 2013; 305(2):C182-9.
7. Attaye I, Smulders Y M, de Waard M C, Oudemans-van Straaten H M, Smit B, Van Wijhe M H, et al. The effects of hyperoxia on microvascular endothelial cell proliferation and production of vaso-active substances. Intensive care medicine experimental. 2017; 5(1):22.
8. Breitzig M, Bhimineni C, Lockey R, Kolliputi N. 4-Hydroxy-2-nonenal: a critical target in oxidative stress? American journal of physiology Cell physiology. 2016; 311(4):C537-C43.
9. Galam L, Failla A, Soundararajan R, Lockey R F, Kolliputi N. 4-hydroxynonenal regulates mitochondrial function in human small airway epithelial cells. Oncotarget. 2015; 6(39):41508-21.
10. Tuder R M, Hunt J M, Schmidt E P. Hyperoxia and apoptosis. Too much of a good thing? American journal of respiratory and critical care medicine. 2011; 183(8):964-5.
11. Waxman A B, Kolliputi N. IL-6 protects against hyperoxia-induced mitochondrial damage via Bcl-2-induced Bak interactions with mitofusins. American journal of respiratory cell and molecular biology. 2009; 41(4):385-96.
12. Chen C H, Budas G R, Churchill E N, Disatnik M H, Hurley T D, Mochly-Rosen D. Activation of aldehyde dehydrogenase-2 reduces ischemic damage to the heart. Science. 2008; 321(5895):1493-5.
13. Neely M D, Sidell K R, Graham D G, Montine T J. The lipid peroxidation product 4-hydroxynonenal inhibits neurite outgrowth, disrupts neuronal microtubules, and modifies cellular tubulin. Journal of neurochemistry. 1999; 72(6):2323-33.
14. Rahman I, van Schadewijk A A, Crowther A J, Hiemstra P S, Stolk J, MacNee W, et al. 4-Hydroxy-2-nonenal, a specific lipid peroxidation product, is elevated in lungs of patients with chronic obstructive pulmonary disease. American journal of respiratory and critical care medicine. 2002; 166(4):490-5.
15. Solito R, Corti F, Chen C H, Mochly-Rosen D, Giachetti A, Ziche M, et al. Mitochondrial aldehyde dehydrogenase-2 activation prevents beta-amyloid-induced endothelial cell dysfunction and restores angiogenesis. Journal of cell science. 2013; 126(Pt 9):1952-61.
16. Galam L, Rajan A, Failla A, Soundararajan R, Lockey R F, Kolliputi N. Deletion of P2X7 attenuates hyperoxia-induced acute lung injury via inflammasome suppression. American journal of physiology Lung cellular and molecular physiology. 2016; 310(6):L572-81.
17. Fukumoto J, Cox R, Jr., Fukumoto I, Cho Y, Parthasarathy P T, Galam L, et al. Deletion of ASK1 Protects against Hyperoxia-Induced Acute Lung Injury. PloS one. 2016; 11(1):e0147652.
18. Perez-Miller S, Younus H, Vanam R, Chen C H, Mochly-Rosen D, Hurley T D. Alda-1 is an agonist and chemical chaperone for the common human aldehyde dehydrogenase 2 variant. Nature structural & molecular biology. 2010; 17(2):159-64.
19. Fu S H, Zhang H F, Yang Z B, Li T B, Liu B, Lou Z, et al. Alda-1 reduces cerebral ischemia/reperfusion injury in rat through clearance of reactive aldehydes. Naunyn-Schmiedeberg's archives of pharmacology. 2014; 387(1): 87-94.
20. Michiels C. Endothelial cell functions. Journal of cellular physiology. 2003; 196(3):430-43.
21. Narala V R, Fukumoto J, Hernandez-Cuervo H, Patil S S, Krishnamurthy S, Breitzig M, et al. Akap1 genetic deletion increases the severity of hyperoxia-induced acute lung injury in mice. American journal of physiology Lung cellular and molecular physiology. 2018; 314(5):L860-L70.
22. Li Y, Liu S-1, Qi S-h. ALDH2 Protects Against Ischemic Stroke in Rats by Facilitating 4-HNE Clearance and AQP4 Down-Regulation. Neurochemical Research. 2018; 43(7):1339-47.
23. Liu M, Lu S, He W, Zhang L, Ma Y, Lv P, et al. ULK1-regulated autophagy: A mechanism in cellular protection for ALDH2 against hyperglycemia. Toxicology letters. 2018; 283:106-15.
24. Ma X, Luo Q, Zhu H, Liu X, Dong Z, Zhang K, et al. Aldehyde dehydrogenase 2 activation ameliorates CCl4-induced chronic liver fibrosis in mice by up-regulating Nrf2/HO-1 antioxidant pathway. Journal of cellular and molecular medicine. 2018.
25. Zhu Q, He G, Wang J, Wang Y, Chen W. Pretreatment with the ALDH2 agonist Alda-1 reduces intestinal injury induced by ischaemia and reperfusion in mice. Clinical science. 2017; 131(11):1123-36.
26. Venugopal R, Galam L, Cox R, Fukumoto J, Cho Y, Parthasarathy P T, et al. Inflammasome Inhibition Suppresses Alveolar Cell Permeability Through Retention of Neuregulin-1 (NRG-1). Cellular physiology and biochemistry: international journal of experimental cellular physiology, biochemistry, and pharmacology. 2015; 36(5):2012-24.
27. Gomes K M, Campos J C, Bechara L R, Queliconi B, Lima V M, Disatnik M H, et al. Aldehyde dehydrogenase 2 activation in heart failure restores mitochondrial function and improves ventricular function and remodelling. Cardiovascular research. 2014; 103(4):498-508.
28. Kolliputi N, Waxman A B. IL-6 cytoprotection in hyperoxic acute lung injury occurs via PI3K/Akt-mediated Bax phosphorylation. American journal of physiology Lung cellular and molecular physiology. 2009; 297(1):L6-16.
29. Xu D, Guthrie J R, Mabry S, Sack T M, Truog W E. Mitochondrial aldehyde dehydrogenase attenuates hyperoxia-induced cell death through activation of ERK/MAPK and PI3K-Akt pathways in lung epithelial cells. American journal of physiology Lung cellular and molecular physiology. 2006; 291(5):L966-75.
30. Hu Y, Yan J B, Zheng M Z, Song X H, Wang L L, Shen Y L, et al. Mitochondrial aldehyde dehydrogenase activity protects against lipopolysaccharideinduced cardiac dysfunction in rats. Molecular medicine reports. 2015; 11(2): 1509-15.

The advantages set forth above, and those made apparent from the foregoing description, are efficiently attained. While the disclosure is susceptible to various modifications and implementation in alternative forms, specific embodiments have been shown by way of non-limiting example in the drawings and have been described in detail herein. Since certain changes may be made in the above construction without departing from the scope of the instant application, it is intended that all matters contained in the foregoing description or shown in the accompanying drawings shall be interpreted as illustrative and not in a limiting sense.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned The disclosure is not intended to be limited to the particular forms disclosed. Rather, the disclosure is to cover all modifications, equivalents, and alternatives falling within the scope of the disclosure as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

It is also to be understood that the following claims are intended to cover all of the generic and specific features of the invention herein described, and all statements of the scope of the invention that, as a matter of language, might be said to fall therebetween.

What is claimed is:

1. A method of preventing hyperoxic acute lung injury in pulmonary cells comprising:
    administering a therapeutically effective amount of a composition to the pulmonary cells comprising
    a therapeutically effective amount of Alda-1; and
    a pharmaceutically acceptable excipient;
    wherein the composition is administered prior to hyperoxic exposure;
    wherein the therapeutically effective amount of the composition containing the Alda-1 reduces damage to the pulmonary cells caused by oxidative stress due to hyperoxic exposure to prevent hyperoxic acute lung injury.

2. The method of claim 1, wherein the administration of the therapeutically effective amount of the composition containing the Alda-1 enhances mitochondrial membrane potential in the pulmonary cells.

3. The method of claim 1, wherein the administration of the therapeutically effective amount of the composition containing the Alda-1 suppresses mitochondrial reactive oxygen species (ROS) production in the pulmonary cells.

4. The method of claim 1, wherein the administration of the therapeutically effective amount of the composition containing the Alda-1 decreases apoptosis of the pulmonary cells.

5. The method of claim 1, wherein the administration of the therapeutically effective amount of the composition containing the Alda-1 decreases accumulation of 4-hydroxy-2-noneal (4HNE) in the pulmonary cells.

6. A method of preventing hyperoxic acute lung injury in pulmonary cells comprising:
    administering a therapeutically effective amount of a composition to the pulmonary cells comprising
    a therapeutically effective amount of Alda-1; and
    a pharmaceutically acceptable excipient;
    wherein the composition is administered during hyperoxic exposure;
    wherein the therapeutically effective amount of the composition containing the Alda-1 reduces damage to pulmonary cells caused by oxidative stress due to hyperoxic exposure to prevent hyperoxic acute lung injury.

7. The method of claim 6, wherein the administration of the therapeutically effective amount of the composition containing the Alda-1 enhances mitochondrial membrane potential in the pulmonary cells.

8. The method of claim 6, wherein the administration of the therapeutically effective amount of the composition containing the Alda-1 suppresses mitochondrial reactive oxygen species (ROS) production in the pulmonary cells.

9. The method of claim 6, wherein the administration of the therapeutically effective amount of the composition containing the Alda-1 decreases apoptosis of the pulmonary cells.

10. The method of claim 6, wherein the administration of the therapeutically effective amount of the composition containing the Alda-1 decreases accumulation of 4-hydroxy-2-noneal (4HNE) in the pulmonary cells.

* * * * *